(12) United States Patent
Witt et al.

(10) Patent No.: US 8,881,900 B2
(45) Date of Patent: Nov. 11, 2014

(54) INSTRUMENT CASE (71) Applicant: Biomet Manufacturing Corporation, Warsaw, IN (US)

(72) Inventors: Tyler D. Witt, Warsaw, IN (US); Jason D. Meridew, Warsaw, IN (US); Thomas J. Mauch, South Bend, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/739,139

(22) Filed: Jan. 11, 2013

(65) Prior Publication Data
US 2014/0197060 A1 Jul. 17, 2014

(51) Int. Cl.
*B65D 81/00* (2006.01)
*A61B 19/02* (2006.01)

(52) U.S. Cl.
CPC .................................. *A61B 19/02* (2013.01)
USPC .......................... 206/370; 220/23.87; 206/363

(58) Field of Classification Search
USPC ......... 206/363, 373, 372, 503, 501, 505, 514, 206/506, 370; 220/23.83, 23.86, 23.87, 220/23.88, 770
See application file for complete search history.

(56) References Cited

U.S. PATENT DOCUMENTS

| | | | |
|---|---|---|---|
| 1,268,124 A * | 6/1918 | Jennings | 206/349 |
| 1,374,849 A | 4/1921 | Greene | |
| 2,364,910 A | 12/1944 | Myrick | |
| 3,392,874 A * | 7/1968 | Meade | 206/514 |
| 3,561,918 A | 2/1971 | Ray | |
| 3,627,122 A * | 12/1971 | Garbe, Jr. | 206/571 |
| 3,628,843 A * | 12/1971 | Wynne et al. | 312/294 |
| 3,743,088 A * | 7/1973 | Henkin | 206/569 |
| 3,780,468 A * | 12/1973 | Maffett | 43/54.1 |
| 4,416,372 A * | 11/1983 | Polk | 206/372 |
| 4,895,256 A * | 1/1990 | Johnston | 206/501 |
| 4,913,309 A | 4/1990 | Fink | |
| D309,519 S * | 7/1990 | Remler | D3/284 |
| 4,958,730 A * | 9/1990 | Bunten | 206/315.11 |
| 5,011,013 A * | 4/1991 | Meisner et al. | 206/373 |
| 5,040,681 A * | 8/1991 | Grusin | 206/503 |
| 5,117,979 A * | 6/1992 | Brightbill | 206/372 |
| 5,117,997 A | 6/1992 | Fink | |
| 5,244,095 A * | 9/1993 | DeVoe | 206/575 |
| 5,384,103 A | 1/1995 | Miller | |
| 5,439,108 A * | 8/1995 | Lackie | 206/373 |
| 5,454,478 A * | 10/1995 | Everson | 220/23.83 |
| 5,494,160 A * | 2/1996 | Gelmetti | 206/395 |
| 5,518,139 A * | 5/1996 | Trower et al. | 220/522 |
| 5,575,401 A * | 11/1996 | Trower et al. | 220/522 |
| D379,562 S * | 6/1997 | Carter | D3/295 |
| 5,680,932 A * | 10/1997 | Dickinson et al. | 206/372 |
| 5,704,158 A * | 1/1998 | Whiteaker | 43/57.1 |
| 5,873,463 A * | 2/1999 | Purcell | 206/372 |
| 5,887,716 A * | 3/1999 | Williams et al. | 206/459.1 |
| 5,992,086 A * | 11/1999 | Cheng | 43/57 |
| D458,448 S | 6/2002 | Jakab | |

(Continued)

*Primary Examiner* — Steven A. Reynolds
(74) *Attorney, Agent, or Firm* — Harness, Dickey (57) ABSTRACT

A surgical instrument tray assembly according to the principles of the present disclosure includes an outer case, an inner tray, and a handle. The inner tray is configured to fit within the outer case and is releasably attached to the outer case. The handle is securely coupled to the inner tray such that the surgical instrument tray assembly, including the outer case and the inner tray, is transportable with a single hand by engaging the handle.

19 Claims, 5 Drawing Sheets

(56) References Cited

U.S. PATENT DOCUMENTS

| | | |
|---|---|---|
| 6,471,060 B1 * | 10/2002 | Leyshon ........................ 206/473 |
| 6,780,383 B1 | 8/2004 | Ettlinger et al. |
| 7,147,829 B2 | 12/2006 | Ettlinger et al. |
| 7,159,714 B2 * | 1/2007 | Wilkinson et al. ............ 206/366 |
| 8,469,195 B2 * | 6/2013 | Gosselink et al. ............ 206/769 |
| 2005/0023167 A1 * | 2/2005 | Yang .............................. 206/373 |
| 2006/0249412 A1 * | 11/2006 | Hernandez et al. ........... 206/379 |
| 2008/0067095 A1 * | 3/2008 | Mueller ........................ 206/373 |

* cited by examiner

*Fig-2*

INSTRUMENT CASE

FIELD

The present disclosure relates to instrument cases, and more particularly, to cases for organizing, storing, cleaning, and/or transporting surgical instruments.

BACKGROUND

This section provides background information related to the present disclosure which is not necessarily prior art.

Surgical instrument trays are used to organize, store, clean, and transport surgical instruments. The trays are generally contained in a case. Surgical instrument trays can contain the tools necessary to prepare, insert, and remove implants such as an acetabular cup. A single implant system can require several trays of instruments to perform these tasks. The multiple trays and/or cases can clutter an operating room and cause delays during surgery as surgical technicians search through multiple trays to find a desired instrument. Although cases with multiple, stackable inner trays have been developed, these cases can be difficult to sort through when searching for a desired instrument.

Handles of instrument trays or cases are typically located at outside ends or sides of the trays or cases. For example, an instrument tray can include one handle attached to one end of the tray and a second handle attached to the opposite end of the tray. Thus, a surgeon or surgical technician must use two hands to lift and move the trays or cases.

SUMMARY

This section provides a general summary of the disclosure, and is not a comprehensive disclosure of its full scope or all of its features.

An example of a surgical instrument tray assembly according to the principles of the present disclosure includes an outer case, an inner tray, and a handle. The inner tray is configured to fit within the outer case and is releasably attached to the outer case. The handle is securely coupled to the inner tray such that the surgical instrument tray assembly, including the outer case and the inner tray, is transportable with a single hand of a user (e.g., a person) by engaging the handle.

An example of a surgical instrument tray assembly according to the principles of the present disclosure includes an outer case, an inner tray, a cover, and a handle. The outer case has a closed bottom and an open top. The inner tray is configured to fit within the outer case and defines a first opening. The cover is configured to cover at least a portion of the open top of the outer case. The cover is releasably attached to the outer case and defines a second opening. The handle is securely coupled to an inner surface of the closed bottom of the outer case. The handle is configured to extend through the first opening in the inner tray and the second opening in the cover such that the outer case, the inner tray, and the cover of the surgical instrument tray assembly are transportable with a single hand by engaging the handle.

An example of a surgical instrument case according to the principles of the present disclosure includes an outer case, an inner cartridge, a case lid, and a handle. The outer case has an open top, a closed bottom, sides extending from the closed bottom, and a plurality of partitions disposed between the sides to define partition areas in an interior of the outer case. The inner cartridge is configured to fit within one of a plurality of the partition areas of the interior of the outer case. The case lid is configured to cover the open top of the outer case and is releasably attached to the outer case. The first handle is coupled to the case lid such that the surgical instrument case is transportable with a single hand by engaging the first handle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

An instrument case according to the principles of the present disclosure can include an outer case, an inner tray, a case lid and/or a handle. The handle can be modular and/or can be rigidly fixed or hinged to the outer case, the inner tray, or the case lid. The handle can be positioned to allow the instrument case to be moved or repositioned using a single hand of a user (e.g., a human person). For example, the handle can be positioned at or near the gravitational center and/or balance point of the instrument case. This configuration makes it easier to find an instrument and thereby reduces delays associated with finding an instrument. In addition, this makes transport of the instrument case efficient for others that may handle the instrument case, such as sales associates selling surgical instruments and/or instrument cases to medical professionals.

Figure 1A:
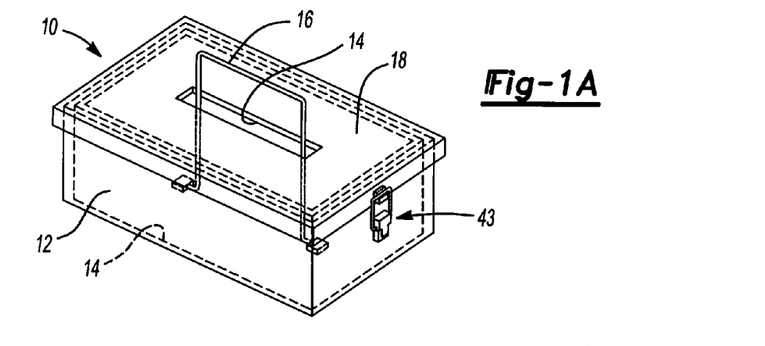
FIG. 1A is a perspective view of a first instrument case according to the principles of the present disclosure.
Figure 1B:
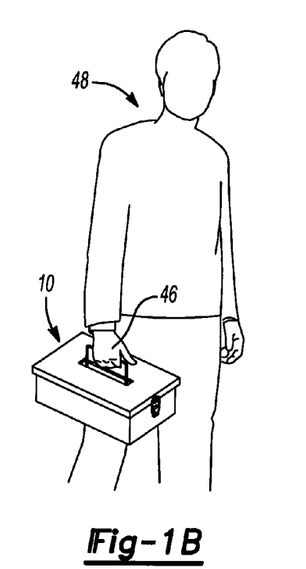
FIG. 1B is a perspective view of a person holding an instrument case according to various embodiments, with one hand.
Figure 2:
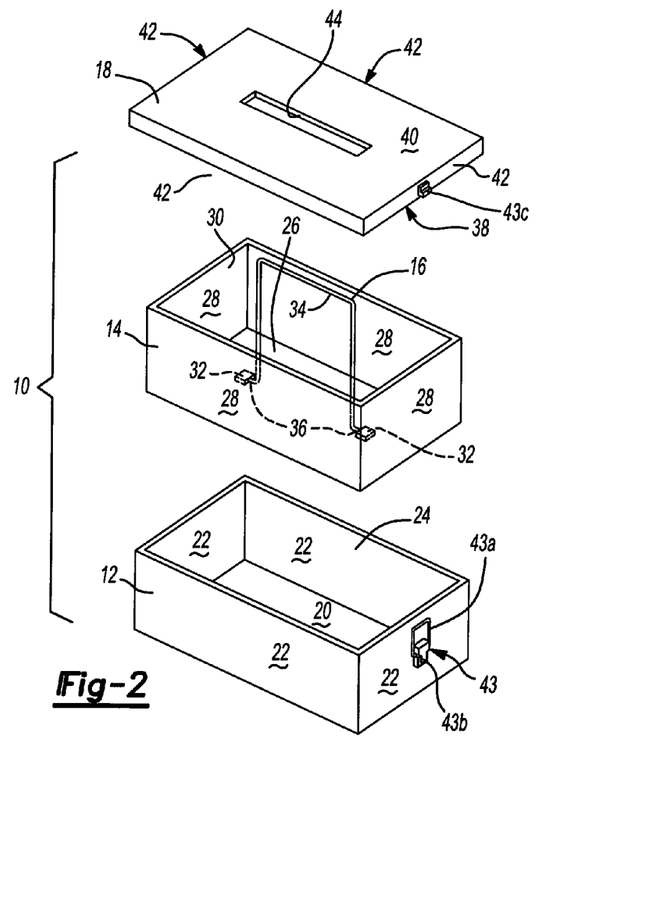
FIG. 2 is an exploded view of the first instrument case of FIG. 1.

Referring now to FIGS. 1A, 1B, and 2, an instrument case 10 includes an outer case 12, an inner tray 14 that is configured to fit within the outer case 12, a handle 16 coupled to the inner tray 14, and a case lid 18. The outer case 12 can form a rectangular box having a floor or bottom 20 closing one end of the outer case 12, sides 22 extending from the bottom 20, and an open top 24. The inner tray 14 can form a rectangular box having a floor or bottom 26 closing one end of the inner tray 14, sides 28 extending from the bottom 26, and an open top 30.

The handle 16 can be modular and/or can be rigidly fixed or hinged to the inner tray 14. The handle 16 can extend beyond the open top 30 of the inner tray 14, such as outside and/or above the sides 28 of the inner tray 14 The handle 16 can include attachment portions 32 and a gripping portion 34. The attachment portions 32 and the gripping portion 34 can be formed as a unitary member or separately formed and connected together. The attachment portions 32 can be attached to the inner surface of the bottom 26 of the inner tray 14. The attachment portions 32 can be attached to the inner tray 14 using fasteners (e.g., rivet, screws) and/or an adhesive.

The gripping portion 34 can be U-shaped with outwardly extending ends 36 and can be rigidly fixed or hinged to the attachment portions 32. The gripping portion 34 can be rigidly fixed to the attachment portions 32 using fasteners and/or an adhesive, or by forming the attachment portions 32 and the gripping portion 34 as a unitary member. The gripping portion 34 can be hinged to the attachment portions 32 by capturing the ends 36 of the gripping portion 34 within the attachment portions 32 while allowing the ends 36 to rotate relative to the attachment portions 32. The gripping portion 34 can also include an ergonomic holding portion, such as a cushioned member.

The case lid 18 can be configured to fit over the open top 24 of the outer case 12 to at least partially enclose the interior of the outer case 12. The case lid 18 can have an open bottom 38, a closed top 40, and sides 42 extending from the closed top 40. The open bottom 38 of the case lid 18 can be configured to receive the open top 24 of the outer case 12 such that the sides 42 of the case lid 18 overlap with the sides 22 of the outer case 12. The case lid 18 can be releasably attached to the outer case 12 using a press or interference fit or a releasable latch 43 (e.g., a locking latch).

The latch 43 can include a first rotating member 43a, a second rotating member 43b, and a keeper or strike 43c. To secure the latch 43, a user can rotate the first rotating member 43a into engagement with the strike 43c, and then rotate the second rotating member 43b toward the outer case 12 to apply tension to the first rotating member 43a. This tension maintains the engagement between the first rotating member 43a and the strike 43c. To release the latch 43, a user can rotate the second rotating member 43b away from the outer case 12 and then rotate the first rotating member 43a out of engagement with the strike 43c.

The closed top 40 of the case lid 18 can define an opening 44. The handle 16 can extend through the opening 44 in the case lid 18 when the case lid 18 is placed on the outer case 12 while the inner tray 14 is disposed within the outer case 12. The handle 16 can be wider at its base (i.e., the region near the attachment portions 32) and narrower at its top to facilitate inserting the handle 16 into and/or through the opening 44 and positioning the case lid 18 on the outer case 12. The size of the opening 44 can be minimized to maximize the portion of the interior of the outer case 12 that is enclosed while still allowing the handle 16 to extend through the opening 44. Also, the opening 44 can include a member to sealingly engage the handle 16 when the case lid 18 is placed on the outer case 12.

The handle 16 can be used to transport the instrument case 10. The handle 16 can be positioned at or near the center of the inner tray 14 such that the instrument case 10 can be transported using a single hand 46 of a user 48 (e.g., a person), as shown in FIG. 1B. As the handle 16 is lifted, the engagement between the sides 28 of the inner tray 14 and the closed top 40 of the case lid 18 lifts the case lid 18. In turn, the engagement between the sides 42 of the case lid 18 and the sides 22 of the outer case 12 (e.g., via a press fit or the latch 43) lifts the outer case 12. Alternatively or additionally, the inner tray 14 can be releasably attached to the outer case 12 using, for example, a press fit, a snap fit, and/or a latch.

Figure 3:
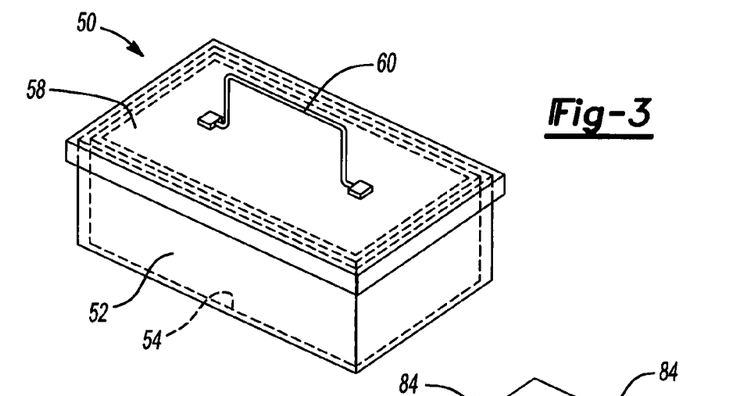
FIG. 3 is a perspective view of a second instrument case according to the principles of the present disclosure.
Figure 4:
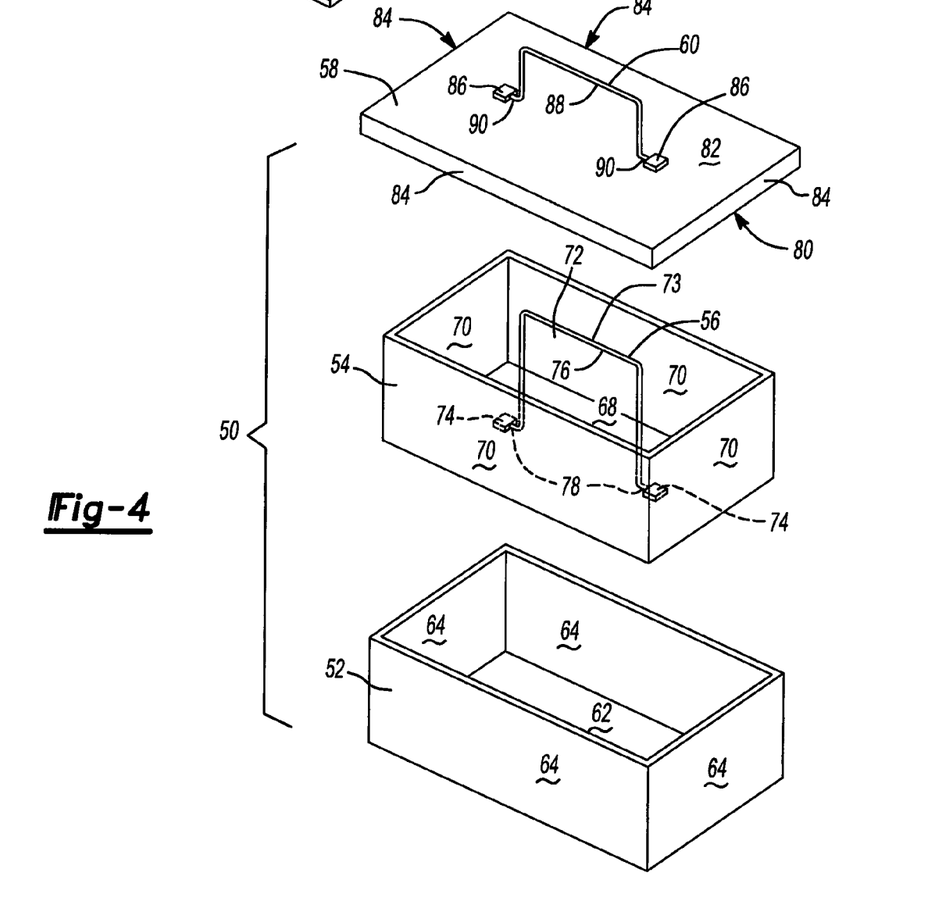
FIG. 4 is an exploded view of the second instrument case of FIG. 3.

Referring now to FIGS. 3 and 4, an instrument case 50 includes an outer case 52, an inner tray 54 configured to fit within the outer case 52, a handle 56 coupled to the inner tray 54, a case lid 58, and a handle 60 coupled to the case lid 58. The outer case 52 can form a rectangular box having a floor or bottom 62 closing one end of the outer case 52, sides 64 extending from the bottom 62, and an open top 66. The inner tray 54 can form a rectangular box having a floor or bottom 68 closing one end of the inner tray 54, sides 70 extending from the bottom 68, and an open top 72.

The handle 56 can be used to lift the inner tray 54. The handle 56 can be modular and/or can be rigidly fixed or hinged to the inner tray 54. A top 73 of the handle 56 can be positioned flush with or below the open top 72 of the inner tray 54. The handle 56 can include attachment portions 74 and a gripping portion 76. The attachment portions 74 and the gripping portion 76 can be formed as a unitary member or separately formed and connected together. The attachment portions 74 can be attached to the inner surface of the bottom 68 of the inner tray 54. The attachment portions 74 can be attached to the inner tray 54 using fasteners and/or an adhesive, as discussed above.

The gripping portion 76 can be U-shaped with outwardly extending ends 78 and can be rigidly fixed or hinged to the attachment portions 74. The gripping portion 76 can be rigidly fixed to the attachment portions 74 using fasteners and/or an adhesive, or by forming the attachment portions 74 and the gripping portion 76 as a unitary member. The gripping portion 76 can be hinged to the attachment portions 74 by capturing the ends 78 of the gripping portion 76 within the attachment portions 74 while allowing the ends 78 to rotate relative to the attachment portions 74.

The case lid 58 can be configured to fit over the open top 66 of the outer case 52 to enclose the interior of the outer case 52. The case lid 58 can form a rectangular box having an open bottom 80, a closed top 82, and sides 84 extending from the closed top 82. The open bottom 80 of the case lid 58 can be configured to receive the open top 66 of the outer case 52 such that the sides 84 of the case lid 58 overlap with the sides 64 of the outer case 52. The case lid 58 can be releasably attached to the outer case 52 using a press or interference fit or a latch, as discussed above.

The handle 60 can be positioned at or near the center of the case lid 58 such that the instrument case 50 can be transported using a single hand of a user. For example, when the case lid 58 is attached to the outer case 52, the handle 60 can be used to move the outer case 52 which can include the inner tray 54. The handle 60 can be modular and/or can be rigidly fixed or hinged to the case lid 58. The handle 60 can include attachment portions 86 and a gripping portion 88. The attachment portions 86 and the gripping portion 88 can be formed as a unitary member or separately formed and connected together. The attachment portions 86 can be attached to the outer surface of the closed top 82 of the case lid 58. The attachment portions 86 can be attached to the case lid 58 using fasteners and/or an adhesive, as discussed above.

The gripping portion 88 can be U-shaped with outwardly extending ends 90 and can be rigidly fixed or hinged to the attachment portions 86. The gripping portion 88 can be rigidly fixed to the attachment portions 86 using fasteners and/or an adhesive, as discussed above, or by forming the attachment portions 86 and the gripping portion 88 as a unitary member. The gripping portion 88 can be hinged to the attachment portions 86 by capturing the ends 90 of the gripping portion 88 within the attachment portions 86 while allowing the ends 90 to rotate relative to the attachment portions 86.

Figures 5, 6:
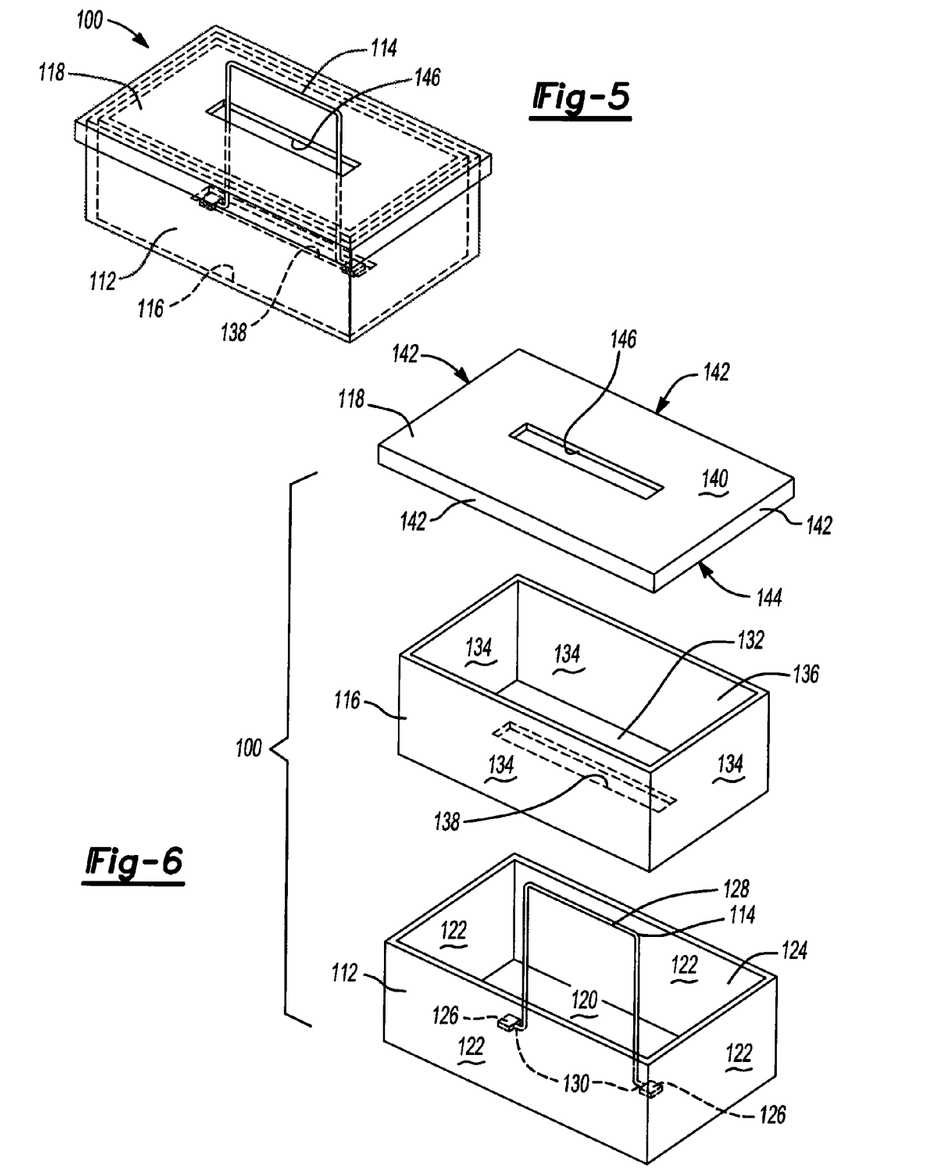
FIG. 5 is a perspective view of a third instrument case according to the principles of the present disclosure.
FIG. 6 is an exploded view of the third instrument case of FIG. 5.

Referring now to FIGS. 5 and 6, an instrument case 100 includes an outer case 112, a handle 114 coupled to the outer case 112, an inner tray 116 configured to fit within the outer case 112, and a cover or case lid 118. The outer case 112 can form a rectangular box having a floor or bottom 120 closing one end of the outer case 112, sides 122 extending from the bottom 120, and an open top 124.

The handle 114 can be modular (i.e., removable from the case 112) and/or can be rigidly fixed or hinged to the bottom 120 of the outer case 112. The handle 114 can include attachment portions 126 and a gripping portion 128. The attachment portions 126 and the gripping portion 128 can be formed as a unitary member or separately formed and connected together. The attachment portions 126 can be attached to the inner surface of the bottom 120 of the outer case 112 using, for example, fasteners and/or an adhesive.

The gripping portion 128 can be U-shaped with outwardly extending ends 130 and can be rigidly fixed or hinged to the attachment portions 126. The gripping portion 128 can be rigidly fixed to the attachment portions 126 using fasteners and/or an adhesive, as discussed above, or by forming the attachment portions 126 and the gripping portion 128 as a unitary member. The gripping portion 128 can be hinged to the attachment portions 126 by capturing the ends 130 of the gripping portion 128 within the attachment portions 126 while allowing the ends 130 to rotate.

The inner tray 116 can form a rectangular box having a floor or bottom 132 at least partially closing one end of the inner tray 116, sides 134 extending from the bottom 132, and an open top 136. The bottom 132 of the inner tray 116 can define an opening 138. The handle 114 can extend through the opening 138 in the inner tray 116 when the inner tray 116 is placed within the outer case 112.

The case lid 118 can be configured to fit over the open top 124 of the outer case 112 to at least partially enclose the interior of the outer case 112. The case lid 118 can have a closed top 140, and sides 142 extending from the closed top 140, and an open bottom 144. The open bottom 144 of the case lid 118 can be configured to receive the open top 124 of the outer case 112 such that the sides 142 of the case lid 118 overlap the sides 122 of the outer case 112. The case lid 118 can be releasably attached to the outer case 112 using a press fit or a latch, as discussed above.

The closed top 140 of the case lid 118 can define an opening 146. The handle 114 can extend through the opening 146 in the case lid 118 when the case lid 118 is placed on the outer case 112. The handle 114 can be wider at its base and narrower at its top to facilitate inserting the handle 114 into the opening 44, positioning the inner tray 116 within the outer case 112, and positioning the case lid 118 on the outer case 112. The size of the opening 146 can be minimized to maximize the portion of the interior of the outer case 112 that is covered while allowing the handle 114 to extend through the opening 146. Also, a sealing member can sealingly engage the handle 114 when the case lid 118 is placed on the outer case 112.

The handle 114 can be used to transport the instrument case 100. The handle 114 can be positioned at or near the center of the outer case 112 such that the instrument case 100 can be transported using a single hand. As the handle 114 is lifted, the engagement between the sides 122 of the outer case 112 and the closed top 140 of the case lid 118 lifts the case lid 118. In addition, the engagement between the bottom 120 of the outer case 112 and the bottom 132 of the inner tray 116 lifts the inner tray 116.

Figures 7, 8:
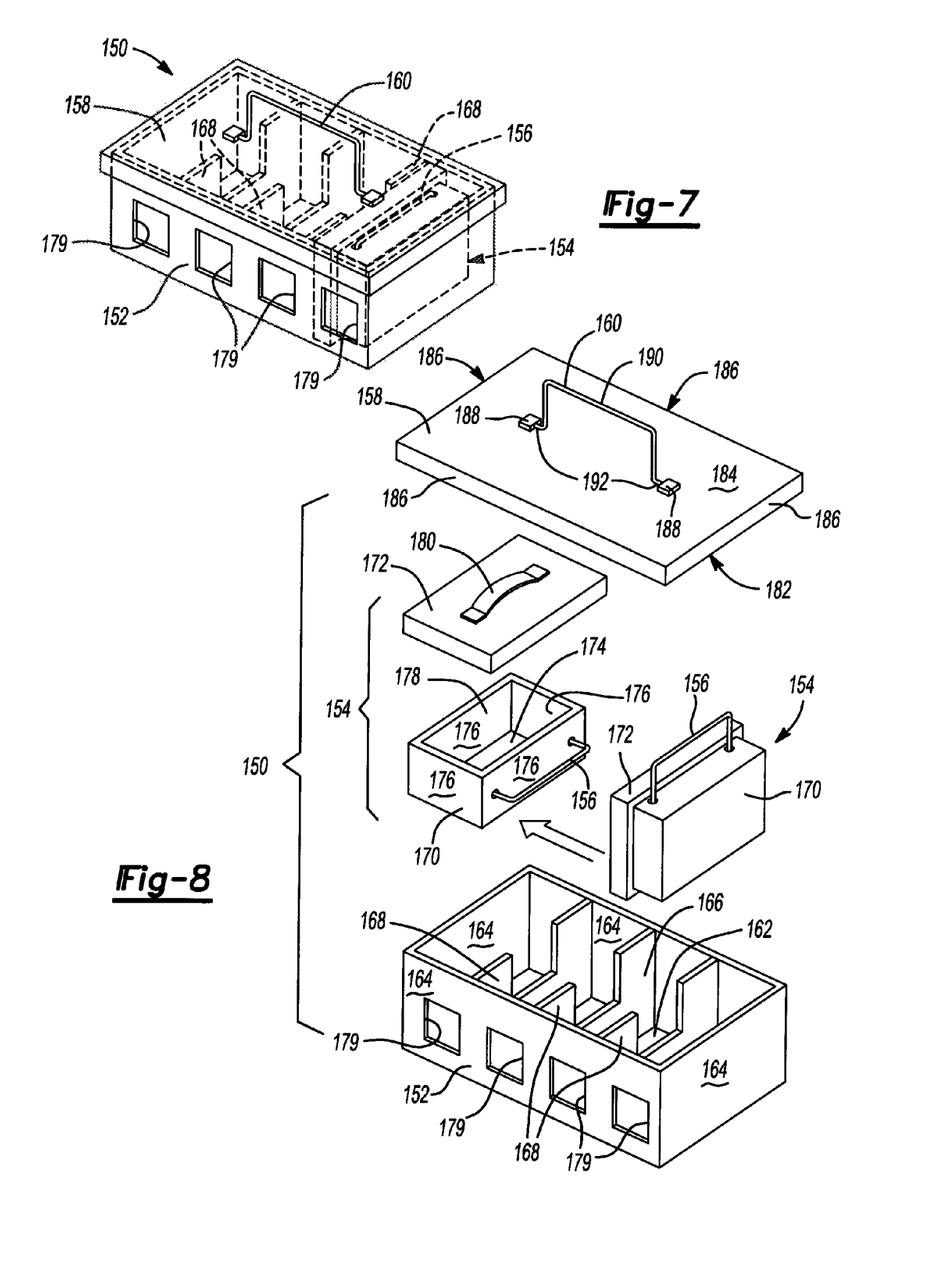
FIG. 7 is a perspective view of a fourth instrument case according to the principles of the present disclosure.
FIG. 8 is an exploded view of the fourth instrument case of FIG. 7 with an inner case of the fourth instrument case assembled and disassembled.

Referring now to FIGS. 7 and 8, an instrument case 150 includes an outer case 152, an inner cartridge 154, a handle 156 coupled to the inner cartridge 154, a case lid 158, and a handle 160 coupled to the case lid 158. The outer case 152 can form a rectangular box having a floor or bottom 162 closing one end of the outer case 152, sides 164 extending from the bottom 162, and an open top 166. The outer case 152 can include a plurality of partitions 168 that partition the interior of the outer case 152. The partitions 168 can be unitarily formed with the remainder of the outer case 152. Alternatively, the partitions 168 can be separately formed and releasably attached to the remainder of the outer case 152. Separately forming the partitions 168 can allow the position of the partitions 168 to be adjusted.

The inner cartridge 154 can be sized to fit within a portion of the interior of the outer case 152 defined by the partitions 168 and the sides 164. Alternatively, the position of the partitions 168 can be adjusted to accommodate the size of the inner cartridge 154. In FIG. 8, the inner cartridge 154 is shown both assembled and disassembled. The instrument case 150 can include multiple inner cartridges that are similar or identical to the inner cartridge 154. The number of inner cartridges may be less than or equal to the number of partitions portions within the interior of the outer case 152.

The inner cartridge 154 can include an inner tray 170 and a cartridge lid 172 that is configured to cover the inner tray 170. The inner tray 170 can form a rectangular box having a floor or bottom 174 closing at least one end of the inner tray 170, sides 176 extending from the bottom 174, and an open top 178. The inner tray 170 can be configured to hold one or more implants and/or tools or tool sets for implants. The tools for implants can include acetabular provisional cups. The tool set can include a plurality of provisional cups that have the same or similar inner diameters and different outer diameters, or vice versa. Each of the inner cartridges 154 can include a full set of tools for an implant. The inner tray 170 can be configured to hold a single type of tool or different types of tools. If the instrument case 150 includes multiple inner cartridges, each inner tray 170 can be configured to hold the same type of tool or different types of tools. Further, all of the inner cartridges 154 in the case 150 can include the same or different tool sets.

The inner tray 170 can be configured to hold a set of tools for a single surgical procedure or for a limited number of surgical procedures. For example, the inner tray 170 can be configured to hold acetabular provisional cups having the same size or a small range of sizes. The size(s) of the acetabular provisional cups, which the inner tray 170 is configured to hold, can be etched or otherwise marked with indicia on one or more of the sides 176 of the inner tray 170. Additionally or alternatively, the inner tray 170 indicia can include a color code to indicate the size(s) of the acetabular provisional cups, which the inner tray 170 is configured to hold. The outer case 152 can define one or more windows 179 so that the indicia on the inner tray 170, such as etching and/or color coding, is visible from outside of the outer case 152 when the inner tray 170 is contained within the outer case 152. The inner tray 170 can be refilled with acetabular provisional cups and resterilized as needed.

The handle 156 can be attached to one of the sides 176 of the inner tray 170. The handle 156 can be used to remove the inner cartridge 154 from the outer case 152. The handle 156 can be modular and removable from the inner cartridge 154 and/or can be rigidly fixed or hinged to the inner cartridge 154 using, for example, fasteners and/or an adhesive. The top of the handle 156 can be positioned flush with or below the open top 166 of the outer case 152 when the inner cartridge 154 is inserted into one of the partitioned portions within the interior of the outer case 152.

The cartridge lid 172 can be releasably attached to the inner tray 170 using a press fit or a latch, as discussed above. The cartridge lid 172 can include a handle 180 that can be used to remove the cartridge lid 172 from the inner tray 170. The handle 180 can be unitarily formed with the remainder of the cartridge lid 172. For example, the handle 180 can be a bump or detent that is formed in the top surface of the cartridge lid 172. Alternatively, the handle 180 can be separately formed and attached to the remainder of the cartridge lid 172 using, for example, fasteners and/or an adhesive.

The case lid 158 can be configured to fit over the open top 166 of the outer case 152 to enclose the interior of the outer case 152. The case lid 158 can form a rectangular box having an open bottom 182, a closed top 184, and sides 186 extending from the closed top 184. The open bottom 182 of the case lid 158 can be configured to receive the open top 166 of the outer case 152 such that the sides 186 of the case lid 158 overlap with the sides 164 of the outer case 152. The case lid 158 can be releasably attached to the outer case 52 using a press fit or a latch.

The handle 160 can be positioned at or near the center of the case lid 158 such that the instrument case 150 can be transported using a single hand of a user. The handle 160 can be modular and/or can be rigidly fixed or hinged to the case lid 158. The handle 160 can include attachment portions 188 and a gripping portion 190. The attachment portions 188 and the gripping portion 190 can be formed as a unitary member or separately formed and connected together. The attachment portions 188 can be attached to the outer surface of the closed top 184 of the case lid 158 using, for example, fasteners and/or an adhesive, as discussed above.

The gripping portion 190 can be U-shaped with outwardly extending ends 192 and can be rigidly fixed or hinged to the attachment portions 188. The gripping portion 190 can be rigidly fixed to the attachment portions 188 using fasteners and/or an adhesive, or by forming the attachment portions 188 and the gripping portion 190 as a unitary member. The gripping portion 190 can be hinged to the attachment portions 188 by capturing the ends 192 of the gripping portion 190 within the attachment portions 188 while allowing the ends 192 to rotate.

Figures 9, 10:
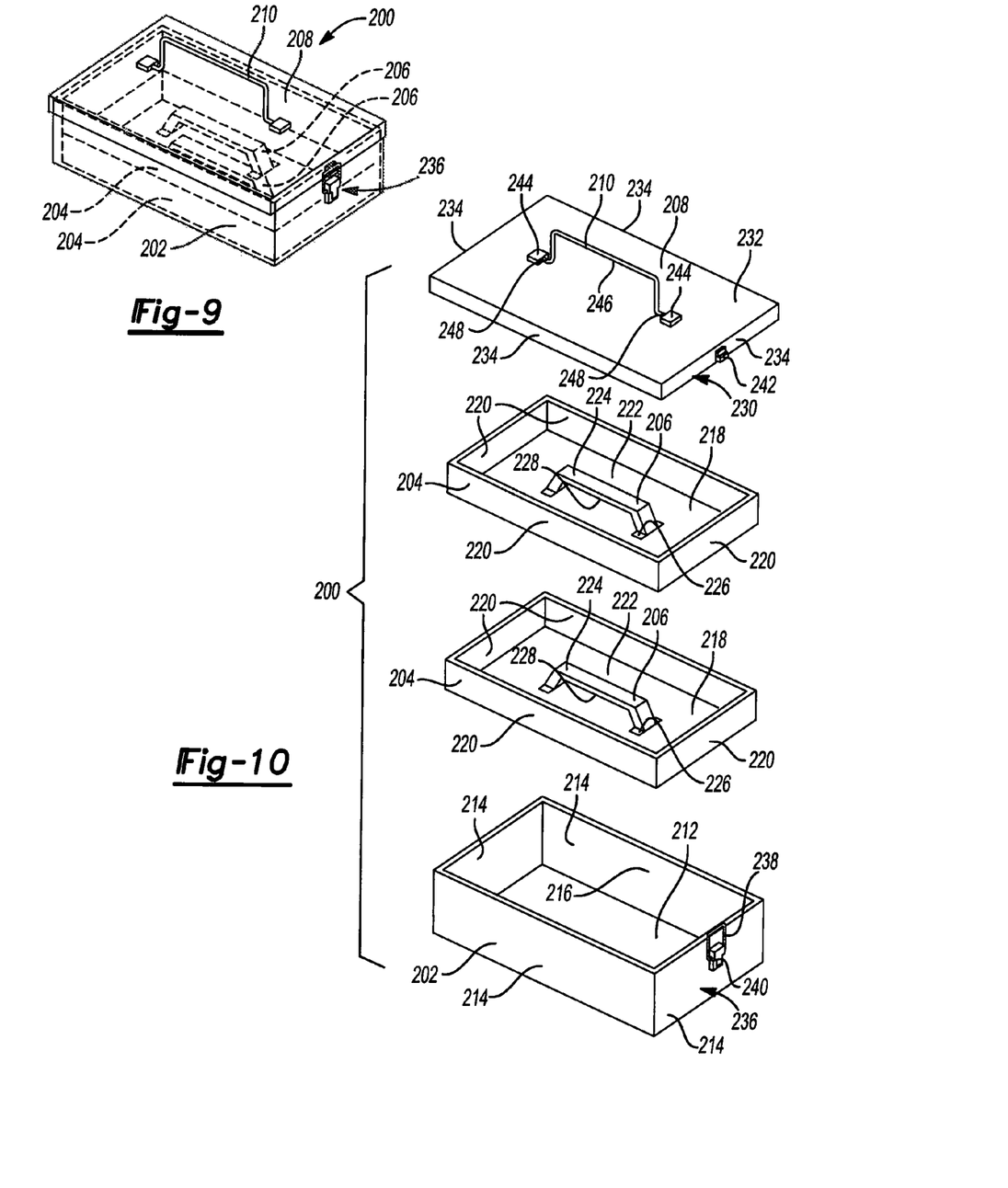
FIG. 9 is a perspective view of a fifth instrument case according to the principles of the present disclosure.
FIG. 10 is an exploded view of the fifth instrument case of FIG. 9.

Referring now to FIGS. 9 and 10, an instrument case 200 includes an outer case 202 and a plurality of stackable inner trays 204 configured to fit within the outer case 202. A handle 206 is coupled to each of the inner trays 204. The instrument case 200 further includes a case lid 208, and a handle 210 is coupled to the case lid 208. The outer case 202 can form a rectangular box having a floor or bottom 212 closing one end of the outer case 202, sides 214 extending from the bottom 212, and an open top 216. Each of the inner trays 204 can form a rectangular box having a floor or bottom 218 closing one end thereof, sides 220 extending from the bottom 218, and an open top 222. It is understood, however, that other geometric shapes can be formed by the outer case 202 and/or the inner trays 204.

The inner trays 204 are configured to be stacked on top of one another. To this end, the inner trays 204 can have the same width and length, and the width and length of the inner trays 204 may be slightly less than the width and length the outer case 202. Thus, as the inner trays 204 are stacked on top of one another within the outer case 202, the sides 214 of the outer case 202 can engage the sides 220 of the inner trays 204 to align the outer perimeters of the inner trays 204. Although only two of the inner trays 204 are shown, the instrument case 200 may include additional ones of the inner trays 204.

The handles 206 can be positioned at or near the centers of inner trays 204. The central handles 206 allow the inner trays 204 to be easily removed from the outer case 202 and transported using a single hand of a user. The handles 206 can be modular to be removably connected to the inner trays 204. In addition or alternatively the handles 206 can be rigidly fixed or hingedly coupled to the inner trays 204. Tops 224 of the handles 206 can be positioned flush with or below the open tops 222 of the inner trays 204. Each of the handles 206 can include attachment portions 226 and a gripping portion 228. The attachment portions 226 and the gripping portion 228 can be unitarily formed or separately formed and connected together. The attachment portions 226 can be attached to the inner surfaces of the bottoms 218 of the inner trays 204 using fasteners and/or an adhesive, as discussed above.

The gripping portions 228 can be rigidly fixed or hinged to the attachment portions 226. The gripping portions 228 can be rigidly fixed to the attachment portions 226 using fasteners and/or an adhesive, or by unitarily forming the attachment portions 226 with the gripping portions 228.

The case lid 208 can be configured to fit over the open top 216 of the outer case 202 to enclose the interior of the outer case 202. The case lid 208 can form a rectangular box having an open bottom 230, a closed top 232, and sides 234 extending from the closed top 232. The open bottom 230 of the case lid 208 can be configured to receive the open top 216 of the outer case 202 such that the sides 234 of the case lid 208 overlap with the sides 214 of the outer case 202. The case lid 208 can be releasably attached to the outer case 202 using a press or interference fit and/or a releasable latch 236 (e.g., a locking latch) disposed on opposite sides of the instrument case 200.

The latch 236 can be a toggle latch that can include a first rotating member 238, a second rotating member 240, and a keeper or strike 242. To secure the latch 236, a user can rotate the first rotating member 238 into engagement with the strike 242, and then rotate the second rotating member 240 toward the outer case 202 to apply tension to the first rotating member 238. This tension maintains the engagement between the first rotating member 238 and the strike 242. To release the latch 236, a user can rotate the second rotating member 240 away from the outer case 202 and then rotate the first rotating member 238 out of engagement with the strike 242.

The handle 210 can be positioned at or near the center of the case lid 208 such that the instrument case 200 can be transported using a single hand of a user. For example, when the case lid 208 is attached to the outer case 202, the handle 210 can be used to move the outer case 202, which may contain the inner trays 204. The handle 210 can be modular such that the handle 210 is efficiently separable form the outer case 202. In addition or alternatively, the handle 210 can be rigidly fixed or hinged to the case lid 208. The handle 210 can include attachment portions 244 and a gripping portion 246. The attachment portions 244 and the gripping portion 246 can be formed as a unitary member or separately formed and connected together. The attachment portions 244 can be attached to the outer surface of the closed top 232 of the case lid 208. The attachment portions 244 can be attached to the case lid 208 using fasteners and/or an adhesive, as discussed above.

The gripping portion 246 can be U-shaped with outwardly extending ends 248 and can be rigidly fixed or hinged to the attachment portions 244. The gripping portion 246 can be rigidly fixed to the attachment portions 244 using fasteners and/or an adhesive, as discussed above, or by forming the attachment portions 244 and the gripping portion 246 as a unitary member. The gripping portion 246 can be hinged to the attachment portions 244 by capturing the ends 248 of the gripping portion 246 within the attachment portions 244 while allowing the ends 248 to rotate relative to the attachment portions 244.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical instrument tray assembly, comprising:
    an outer case having an open top;
    an inner tray configured to fit entirely within an interior of the outer case, the inner tray being releasably attached to the outer case;
    a case lid configured to at least partially cover the open top of the outer case, the case lid being releasably attached to the outer case; and
    a first handle hinged to the inner tray and configured to extend through the case lid when the case lid is releasably attached to the outer case such that the surgical instrument tray assembly, including the outer case and the inner tray, is transportable with a single hand by engaging the first handle.

2. The surgical instrument tray assembly of claim 1, wherein the first handle is coupled to the center of the inner tray.

3. The surgical instrument tray assembly of claim 1, wherein the first handle is attached to an inner surface of a closed bottom of the inner tray.

4. The surgical instrument tray assembly of claim 3, wherein the first handle is configured to extend away from the closed bottom and beyond an open top of the inner tray.

5. The surgical instrument tray assembly of claim 1, wherein the case lid defines an opening and the first handle extends through the opening when the inner tray is disposed within the outer case and the case lid is placed over the open top of the outer case.

6. A surgical instrument tray assembly, comprising:
    an outer case having a closed bottom and an open top;
    an inner tray configured to fit entirely within an interior of the outer case, the inner tray defining a first opening;
    a cover configured to cover at least a portion of the open top of the outer case, the cover being releasably attached to the outer case, the cover defining a second opening; and
    a handle securely coupled to an inner surface of the closed bottom of the outer case and configured to extend through the first opening in the inner tray and the second opening in the cover such that the outer case, the inner tray, and the cover of the surgical instrument tray assembly are transportable with a single hand by engaging the handle.

7. The instrument tray assembly of claim 6, wherein the handle includes a single gripping portion and a base of the handle has a first width and a top of the handle has a second width that is less than the first width.

8. The instrument tray assembly of claim 6, wherein the handle is positioned at a center of the closed bottom of the outer case.

9. The instrument tray assembly of claim 8, wherein the handle is formed as a single unit and rigidly fixed to the inner surface of the closed bottom of the outer case.

10. The instrument tray assembly of claim 6, wherein the handle is hinged to the inner surface of the closed bottom of the outer case.

11. The instrument tray assembly of claim 10, wherein the handle includes attachment portions that are fixed to the closed bottom of the outer case and a single gripping portion that is rotatably coupled to the attachment portions.

12. A surgical instrument case, comprising:
    an outer case having an open top, a closed bottom, sides extending from the closed bottom, and a plurality of partitions extending from the sides to define a plurality of partition areas in an interior of the outer case;
    an inner cartridge configured to fit within one of the plurality of partition areas of the interior of the outer case defined by the closed bottom of the outer case, wherein the inner cartridge includes an inner tray and a cartridge lid that is configured to cover an open top of the inner tray;
    a case lid configured to cover the open top of the outer case, the entire case lid being releasably attached to the outer case; and
    a first handle coupled to the case lid such that the surgical instrument case is transportable with a single hand by engaging the first handle.

13. The surgical instrument case of claim 12, wherein the inner cartridge has an external geometry configured to fit within one of the plurality of partition areas.

14. The surgical instrument case of claim 13, wherein the inner tray has the open top, a closed bottom, and sides extending from the closed bottom, the surgical instrument case further comprising a second handle attached to one of the sides of the inner tray.

15. The surgical instrument case of claim 13, further comprising a second handle attached to an outer surface of a closed top of the cartridge lid.

16. The surgical instrument case of claim 13, wherein the inner tray is configured to hold a set of surgical tools relating to a single selected procedure.

17. The surgical instrument case of claim 16, wherein the inner tray includes indicia indicating at least one size of the set of surgical tools which the inner tray is configured to hold.

18. The surgical instrument case of claim 17, wherein the set of surgical tools includes at least one acetabular provisional cup.

19. The surgical instrument case of claim 17, wherein the outer case defines a window to make the indicia visible from outside of the outer case.

* * * * *

UNITED STATES PATENT AND TRADEMARK OFFICE
CERTIFICATE OF CORRECTION

PATENT NO.        : 8,881,900 B2
APPLICATION NO.   : 13/739139
DATED             : November 11, 2014
INVENTOR(S)       : Tyler D. Witt et al.

Page 1 of 1

It is certified that error appears in the above-identified patent and that said Letters Patent is hereby corrected as shown below:

In the Specification,

Column 3, Line 26, After "14", insert --.--.

Column 7, Line 55, Delete "52" and insert --152--.

Signed and Sealed this
Seventh Day of April, 2015

Michelle K. Lee
*Director of the United States Patent and Trademark Office*